(12) United States Patent
Meignant

(10) Patent No.: US 9,360,444 B2
(45) Date of Patent: Jun. 7, 2016

(54) FLUID SENSOR AND METHOD OF USING SAME

(75) Inventor: Didier Meignant, Grasse (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 299 days.

(21) Appl. No.: 13/579,941

(22) PCT Filed: Feb. 7, 2011

(86) PCT No.: PCT/EP2011/000556
§ 371 (c)(1),
(2), (4) Date: Oct. 17, 2012

(87) PCT Pub. No.: WO2011/101100
PCT Pub. Date: Aug. 25, 2011

(65) Prior Publication Data
US 2013/0027042 A1    Jan. 31, 2013

(30) Foreign Application Priority Data

Feb. 19, 2010 (EP) ..................................... 10290083

(51) Int. Cl.
G01V 3/20 (2006.01)
G01N 27/06 (2006.01)
G01N 33/28 (2006.01)

(52) U.S. Cl.
CPC ............ G01N 27/06 (2013.01); G01N 33/2823 (2013.01)

(58) Field of Classification Search
CPC .......... G01N 33/2823; G01N 33/2888; G01N 27/02; G01N 27/06; G01N 27/07; G01N 27/226; G01N 33/26; G01N 33/28; G01N 27/04; G01N 27/22; G01N 27/228
USPC .................. 324/324, 439, 446, 693, 698, 724
See application file for complete search history.

(56) References Cited

U.S. PATENT DOCUMENTS

| | | | |
|---|---|---|---|
| 4,608,983 A | | 9/1986 | Muller et al. |
| 5,005,409 A | * | 4/1991 | Hochstein .................. 73/304 C |
| 5,042,299 A | * | 8/1991 | Wells .................... G01F 23/268 324/663 |
| 5,457,396 A | | 10/1995 | Mori et al. |
| 5,889,200 A | * | 3/1999 | Centers et al. ............... 73/53.01 |
| 6,173,793 B1 | * | 1/2001 | Thompson et al. ............. 175/45 |
| 6,377,052 B1 | * | 4/2002 | McGinnis et al. ............ 324/446 |
| 6,527,923 B2 | | 3/2003 | Kirk et al. |

(Continued)

FOREIGN PATENT DOCUMENTS

| | | |
|---|---|---|
| DE | 19649366 | 5/1999 |
| EP | 1467060 | 10/2004 |

(Continued)

*Primary Examiner* — Tung X Nguyen
*Assistant Examiner* — David Frederiksen

(57) ABSTRACT

A fluid sensor and method for determining at least one parameter of a fluid of a wellbore is provided. The fluid sensor has a base positionable on a downhole tool and a pair of electrodes. The base is provided with insulation. The pair of electrodes is operatively positioned in the insulation. The pair of electrodes has a space therebetween for passage of the wellbore fluid therethrough. A first of the pair of electrodes is interlaced with a second of the pair of electrodes such that at least a portion of the second of the pair of electrodes is surrounded by the first of the pair of electrodes. A voltage applied across the pair of electrodes generates a current therebetween whereby at least one parameter of the wellbore fluid may be determined. The fluid sensor is deployable into the wellbore via the downhole tool.

15 Claims, 3 Drawing Sheets

(56) References Cited

U.S. PATENT DOCUMENTS

| | | |
|---|---|---|
| 6,801,039 B2 | 10/2004 | Fabris et al. |
| 7,258,005 B2 | 8/2007 | Nyee |
| 7,905,145 B2 * | 3/2011 | Naydenov ............. G01F 23/266 324/663 |
| 2002/0153897 A1 * | 10/2002 | Evans et al. ................... 324/374 |
| 2003/0000303 A1 * | 1/2003 | Livingston et al. ......... 73/304 C |
| 2004/0178069 A1 | 9/2004 | Wang et al. |
| 2005/0040035 A1 * | 2/2005 | Mpholo et al. ................ 204/288 |
| 2005/0103624 A1 * | 5/2005 | Bhullar et al. ........... 204/403.01 |
| 2007/0206440 A1 * | 9/2007 | Fripp et al. ....................... 367/81 |
| 2008/0303525 A1 * | 12/2008 | Itskovich et al. .............. 324/351 |
| 2009/0008079 A1 * | 1/2009 | Zazovsky et al. ............... 166/60 |
| 2009/0090176 A1 | 4/2009 | Toribio et al. |
| 2009/0153155 A1 | 6/2009 | Chambon et al. |
| 2009/0204346 A1 | 8/2009 | Xie |
| 2010/0299068 A1 * | 11/2010 | Mason et al. ...................... 702/7 |
| 2011/0107833 A1 * | 5/2011 | Thibault ..................... 73/304 C |
| 2011/0113878 A1 * | 5/2011 | Ohshima et al. ............. 73/304 C |
| 2011/0120219 A1 * | 5/2011 | Barlesi ................. G01F 23/266 73/304 C |

FOREIGN PATENT DOCUMENTS

| | | | |
|---|---|---|---|
| GB | 2313196 | 11/1997 | |
| WO | WO 2010010683 A1 * | 1/2010 | ............. G01F 23/26 |

\* cited by examiner

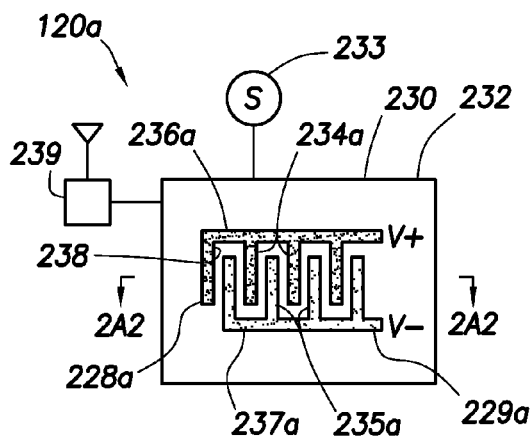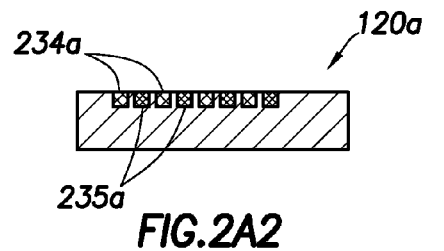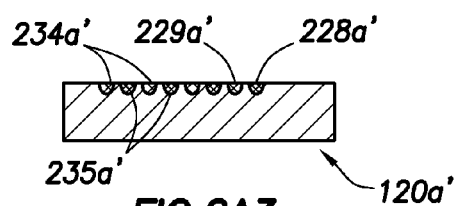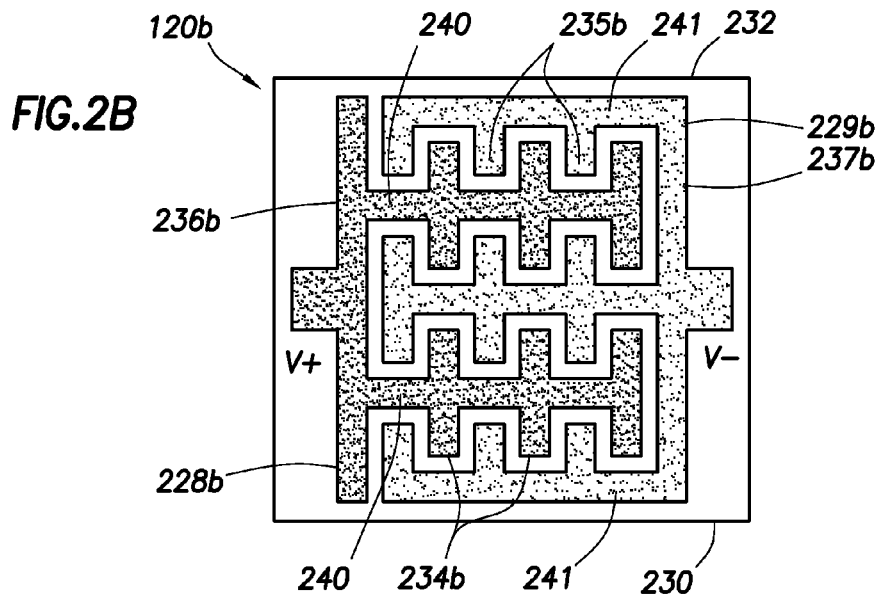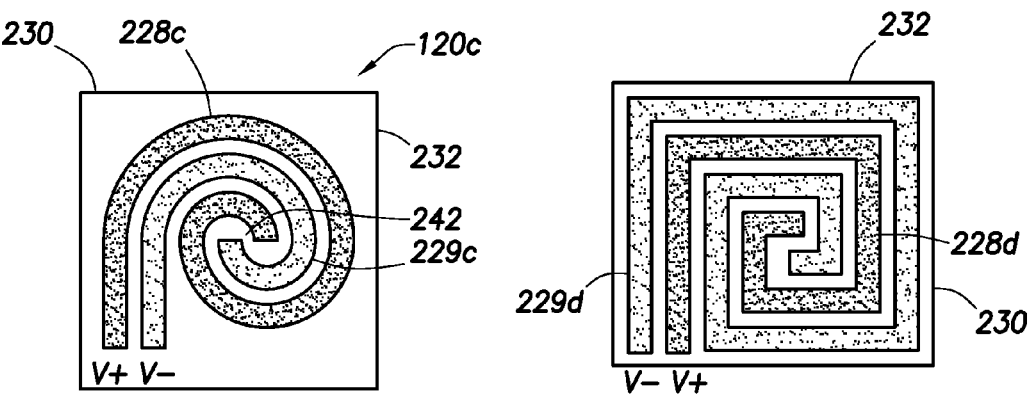

FLUID SENSOR AND METHOD OF USING SAME

BACKGROUND OF THE INVENTION

1. Field of the Invention

The present invention relates to techniques for determining fluid parameters. More particularly, the present invention relates to techniques for determining electrical parameters of downhole fluids.

2. Background of the Related Art

Oil rigs are positioned at wellsites for performing a variety of oilfield operations, such as drilling a wellbore, performing downhole testing and producing located hydrocarbons. Downhole drilling tools are advanced into the earth from a surface rig to form a wellbore. Drilling muds are often pumped into the wellbore as the drilling tool advances into the earth. The drilling muds may be used, for example, to remove cuttings, to cool a drill bit at the end of the drilling tool and/or to provide a protective lining along a wall of the wellbore. During or after drilling, casing is typically cemented into place to line at least a portion of the wellbore. Once the wellbore is formed, production tools may be positioned about the wellbore to draw fluids to the surface.

During drilling, measurements are often taken to determine downhole conditions. In some cases, the drilling tool may be removed so that a wireline testing tool may be lowered into the wellbore to take additional measurements and/or to sample downhole fluids. Once the drilling operation is complete, production equipment may be lowered into the wellbore to assist in drawing the hydrocarbons from a subsurface reservoir to the surface.

The downhole measurements taken by the drilling, testing, production and/or other wellsite tools may be used to determine downhole conditions and/or to assist in locating subsurface reservoirs containing valuable hydrocarbons. Such wellsite tools may be used to measure downhole parameters, such as temperature, pressure, viscosity, resistivity, etc. Such measurements may be useful in directing the oilfield operations and/or for analyzing downhole conditions.

In particular, it is often desirable to determine what types of fluids are present in the wellbore. Various techniques have been developed for measuring wellbore fluids as described, for example, in US Patent/Application No. 20090204346. Techniques have also been developed for using electrodes in downhole tools as described, for example, in US Patent/Application No. 20090090176 and 6801039. In some cases, electrodes have been used for measuring fluid properties as described, for example, in US Patent/Application Nos. 20090153155, 7258005, 5457396, 6527923, and 4608983.

Despite the development of techniques for measuring wellbore fluids and/or in the use of electrodes, there remains a need to provide advanced techniques for determining parameters of wellbore fluids using wellsite tools. It may be desirable to provide techniques that enhance downhole fluid measurements. It may be further desirable to provide techniques that reduce the effects of other components, such as conductive components, that may interfere with measurements. Preferably, such techniques involve one or more of the following, among others: accuracy of measurements, optimized measurement processes, reduced clogging, minimized components, reduced size, increased surface area for measurement, constant flow of fluids during measurement, optimized shape of measurement apparatus/system, real time capabilities, compatibility with existing wellsite equipment, operability in downhole conditions (e.g., at high temperatures and/or pressures), etc.

SUMMARY OF THE INVENTION

The present invention relates to a fluid sensor for determining at least one parameter of a fluid of a wellbore. The fluid sensor comprises a base positionable in the wellbore, and a pair of electrodes. The base comprises insulation. The pair of electrodes is operatively positioned in the insulation. The pair of electrodes has a space therebetween for passage of the wellbore fluid therethrough. A first of the pair of electrodes is interlaced with a second of the pair of electrodes such that at least a portion of the second of the pair of electrodes is surrounded by the first of the pair of electrodes. A voltage applied across the pair of electrodes generates a current therebetween whereby at least one parameter of the wellbore fluid may be determined.

The present invention also relates to a system for determining at least one parameter of a fluid in a wellbore. The system includes a downhole tool positionable in the wellbore and a fluid sensor. The fluid sensor comprises a base positionable on the downhole tool, and a pair of electrodes. The base comprises insulation. The pair of electrodes is operatively positioned in the insulation. The pair of electrodes has a space therebetween for passage of the wellbore fluid therethrough. A first of the pair of electrodes is interlaced with a second of the pair of electrodes such that at least a portion of the second of the pair of electrodes is surrounded by the first of the pair of electrodes. A voltage applied across the pair of electrodes generates a current therebetween whereby at least one parameter of the wellbore fluid may be determined.

Finally, the present invention relates to a method for determining at least one parameter of a fluid in a wellbore. The method involves providing a fluid sensor, positioning a downhole tool into the wellbore with the fluid sensor thereon, receiving a downhole fluid between the pair of electrodes, applying a voltage across the pair of electrodes to generate a current therebetween, and determining the at least one fluid parameter from the generated current. The fluid sensor comprises a base positionable in the wellbore and a pair of electrodes. The base comprises insulation. The pair of electrodes is operatively positioned in the insulation. The pair of electrodes has a space therebetween for passage of the wellbore fluid therethrough. A first of the pair of electrodes is interlaced with a second of the pair of electrodes such that at least a portion of the second of the pair of electrodes is surrounded by the first of the pair of electrodes. A voltage applied across the pair of electrodes generates a current therebetween whereby at least one parameter of the wellbore fluid may be determined.

BRIEF DESCRIPTION OF THE DRAWINGS

So that the features and advantages of the present invention can be understood in detail, a more particular description of the invention may be had by reference to the embodiments thereof that are illustrated in the appended drawings. These drawings are used to illustrate only typical embodiments of this invention, and are not to be considered limiting of its scope, for the invention may admit to other equally effective embodiments. The figures are not necessarily to scale and certain features and certain views of the figures may be shown exaggerated in scale or in schematic in the interest of clarity and conciseness.

FIGS. 2A-2D are schematic views of the fluid sensor of FIG. 1. FIGS. 2A1-2A3 show views of a fluid sensor with electrodes in a complimentary, dual-comb configuration. FIG. 2B shows a fluid sensor with electrodes in an interlocked, multi-comb configuration. FIG. 2C shows a fluid sensor with electrodes in an interlocked, round spiral configuration. FIG. 2D shows a fluids sensor with electrodes in an interlocked, square spiral configuration.

FIG. 3 is a flow chart depicting a method of determining downhole fluid parameters.

DETAILED DESCRIPTION OF THE INVENTION

Presently preferred embodiments of the invention are shown in the above-identified Figures and described in detail below.

Figure 1:
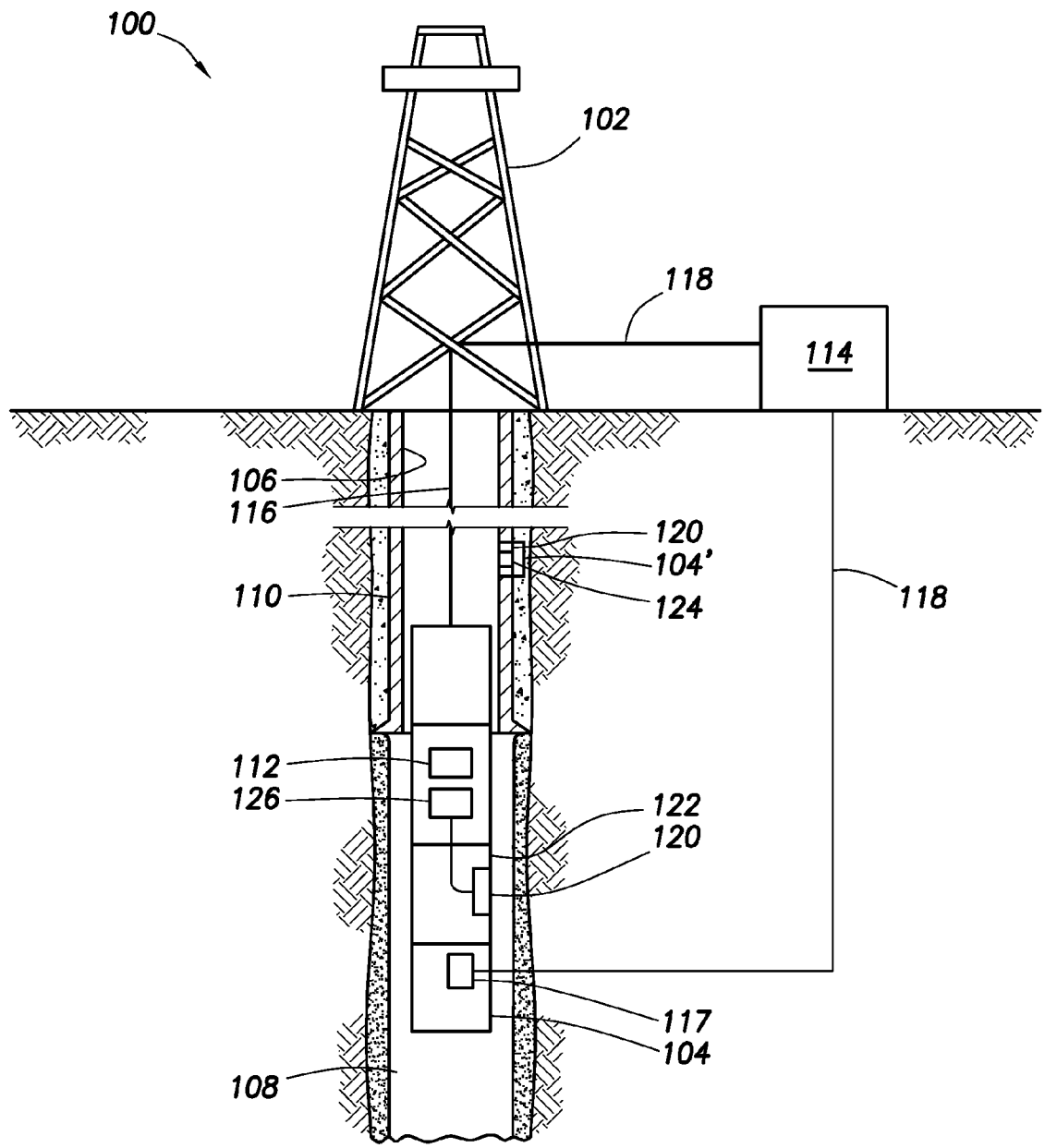
FIG. 1 is a schematic depiction of a system for determining downhole fluid parameters comprising a downhole tool positioned in a wellbore, and a fluid sensor on the downhole tool for determining fluid parameters.

FIG. 1 is a schematic view of a wellsite 100 having an oil rig 102 with a downhole tool 104 suspended into a wellbore 106 therebelow. The wellbore 106 has been drilled by a drilling tool (not shown). A drilling mud 108 has been pumped into the wellbore 106 and lines a wall thereof. A casing 110 has also been positioned in the wellbore 106 and cemented into place therein.

The downhole tool 104 is shown as a wireline logging tool lowered into the wellbore 106 to take various measurements. The downhole tool 104 has a conventional logging device 112 therein that may be provided with various sensors, measurement devices, communication devices, sampling devices and/or other devices for performing wellbore operations. For example, as the downhole tool 104 is lowered, it may use devices known in the art, such as resistivity or other logging devices, to measure formation properties.

The downhole tool 104 is operatively connected to a surface unit 114 for communication therebetween. The downhole tool 104 may be wired via the wireline 116 as shown and/or wirelessly linked via telemetry devices 117, such as conventional electromagnetic devices known in the art, for passing signals to a surface unit 114 as indicated by communication links 118. Signals may be passed between the downhole tool 104 and the surface unit 114 and/or other locations for communication therebetween.

The downhole tool 104 is also provided with a fluid sensor 120 for determining downhole fluid parameters. The fluid sensor 120 is preferably capable of determining parameters of downhole fluids, such as downhole mud (e.g., oil based), hydrocarbons, water and/or other downhole fluids. Additionally, the fluid sensor 120 is preferably capable of determining parameters of downhole fluids as the downhole tool 104 passes through the wellbore 106. Due to the harsh conditions of the downhole environment, the fluid sensor 120 is preferably positioned on the downhole tool 104 in such a manner that the fluid sensor is capable of receiving fluids as the downhole tool 104 passes through the wellbore 106, and that reduces clogging of such fluids as fluids pass through the fluid sensor 120. As shown, the fluid sensor 120 is positioned on an outer surface 122 of the downhole tool 104. The fluid sensor 120 may be recessed a distance below the outer surface 122 to provide additional protection thereto, or protruded a distance therefrom to access fluid. The fluid sensor 120 may also be positioned at various angles as desired.

The fluid sensor 120 is also depicted as being positioned on production monitoring devices 104'. The production monitors 104' may be conventional production monitors as known in the art. These production monitors 104' are typically positioned about the well as shown for monitoring the production of fluids through the wellbore 106. The fluid sensors 120 are positioned on an outer surface 124 of one or more of the production monitors 104'.

While the downhole tool 104 is depicted as a wireline tool 104 and a production monitor 104' with the fluid sensor 120 thereon, it will be appreciated that the fluid sensor 120 may be positioned downhole on a variety of one or more tools. For example, the fluid sensor 120 may be placed downhole on a drilling, coiled tubing, drill stem tester, production, casing, pipe, or other downhole tool. The fluid sensor 120 is preferably positioned about an outer surface of the downhole tool so that fluid may pass therealong for measurement thereof. However, it will be appreciated that one or more fluid sensors 120 may be positioned at various locations about the wellsite as desired for performing fluid measurement.

A power source 126 is operatively connected to the fluid sensor 120 for applying a voltage thereto. The power source 126 may be provided by a battery, power supply or other conventional means of providing power. In some cases, the power source 126 may be an existing power source used in the downhole tool. The power source 126 may be positioned, for example, in the downhole tool 104 and wired to the fluid sensor 120 for providing power thereto as shown. Optionally, the power source 126 may be provided for use with the fluid sensor 120 and/or other downhole devices. The power source 126 may be positioned within the fluid sensor 120 or separate therefrom. The fluid sensor 120 may also be wired or wirelessly connected to other features of the downhole tool, such as communication links, processors, power sources or other features thereof.

FIGS. 2A-2D show detailed views of various configurations 120a-d usable as the fluid sensor 120 of FIG. 1. Each fluid sensor 120a-d comprises a pair of folded electrodes 228a-d, 229a-d positioned in insulation 230 on a base (or pad) 232. Part or all of the base 232 may comprise the insulation 230. The base 232 may be adhered to the outer surface 122 of the downhole tool (e.g., 104 and/or 104' in FIG. 1) using any conventional means. The insulation 230 may be adhered to the base 232 using any conventional means. The insulation 230 is preferably a material, such as a polymide resin, capable of providing insulation about the electrodes 228a-d,229a-d. The insulation 230 may be provided with a thin layer of copper thereon, and with a layer of gold applied to the copper to prevent oxidation (not shown). The electrodes 228a-d, 229a-d may be applied into the insulation 230 in the desired configuration using, for example, printed circuit board technology, wet or dry etching, and/or other conventional electronics construction technique.

The electrodes 228a-d,229a-d may be any conventional electrode capable of generating current across a fluid. A power source (e.g., power source 126 of FIG. 1) is operatively connected to the electrodes 228a-d,229a-d for applying a voltage (V+, V−) thereacross as schematically depicted. The electrodes 228a-d,229a-d are combined to form a capacitor for measuring current flowing therebetween. The electrodes 228a-d,229a-d are preferably positioned such that capacitances are achieved between the surfaces of the electrodes 228a-d,229a-d as wellbore fluids pass therebetween. As voltage is applied, a current flows out of one of the electrodes that can be measured.

The current from the electrodes may be used to determine various parameters. In an example involving a fluid passing between a pair of electrodes, an AC voltage V is applied between two parallel plates to generate a resultant current I that can be measured at either electrode. An impedance generated from the electrodes may consist of two capacitances in parallel, such as the capacitances between the electrodes interfacing with the wellbore fluid and interfacing with the insulation. The complex impedance Z can determined from the measured current I based on the following:

$$Z=|Z|\exp(i\phi_Z) \quad \text{Equation (1)}$$

where its magnitude |Z| based on Ohms law and phase $\phi_Z$ are defined as follows:

$$|Z|=|V/I| \quad \text{Equation (2)}$$

$$\phi_Z=\text{phase of I relative V} \quad \text{Equation (3)}$$

and where exp $(i\phi_Z)$ based on Euler's formula is defined as follows:

$$\exp(i\phi_Z)=\sin\phi_Z+i\cos\phi_Z \quad \text{Equation (4)}$$

The magnitude and phase of the impedivity (sometimes referred to as the complex impedivity) of a fluid $\zeta$ is defined as follows:

$$\zeta=|\zeta|\exp(i\phi_\zeta) \quad \text{Equation (5)}$$

Equation (5) may be derived from Z by the relations as follows:

$$|\zeta|=k|Z| \quad \text{Equation (6)}$$

Equation (6) may also be written as follows:

$$|\zeta|=k|V|/|I| \quad \text{Equation (7)}$$

The phase (or dielectric angle) of the fluid $\zeta$, is derived as follows:

$$\phi_\zeta=\phi_Z \quad \text{Equation (8)}$$

where:
|ζ| is the magnitude of impedivity,
$\phi_\zeta$ is the phase angle of the impedivity, and
k is a constant for the device.

The constant k may be measured empirically, for example, by measuring the impedance V/I between electrodes as a fluid of known impedivity is passed therethrough. The constant k may also be calculated from the geometry et of the electrodes using conventional methods.

Data concerning the measured current may be used to determine fluid parameters, such as impedivity, resistivity, impedance, general conductivity, complex conductivity, complex permittivity, tangent delta, and combinations thereof, as well as other parameters of the wellbore fluid. The data may be analyzed to determine characteristics of the wellbore fluid, such as the type of fluid (e.g., hydrocarbon, mud, contaminants, etc.) A processor (e.g., logging device 112 of FIG. 1) may be used to analyze the data. Optionally, the data may be communicated to the surface unit 114 and/or other location for storage and/or analysis. Such analysis may be performed with other inputs, such as historical or measured data about this or other wellsites. Reports and/or other outputs may be generated from the data. The data may be used to make decisions and/or adjust operations at the wellsite. In some cases, the data may be fed back to the wellsite for real-time decision making and/or operation.

Preferably, the electrodes 228,229 of the fluid sensor 120 are configured to optimize measurement of fluid passing therebetween. The base is preferably of a small dimension having a surface area of about 1 cm². The space between the electrodes preferably has a width of about 100 µm. Up to about fifty percent (50%) of the surface of the electrodes is preferably exposed to wellbore fluids.

As shown in FIGS. 2A-2D, the electrodes 228a-d,229a-d are in a folded configuration to enhance the interaction therebetween. In each case, the electrodes 228a-d, 229a-d are interlaced such that a first electrode surrounds at least a portion of the second electrode. In FIG. 2A, the electrodes 228a, 229a are positioned in a complimentary configuration adjacent to each other. In FIGS. 2B-2D, the electrodes 228b-d, 229b-d are in an interlocked configuration with a first electrode wrapped around a second electrode.

A voltage may be applied across the electrodes 228a-d, 229a-d as shown. The voltage may be, for example, an AC voltage signal at a high frequency of between about 1 kHz and 200 MHz. The electrodes 228a-d,229a-d are preferably positioned with a small space therebetween of about 4 to about 40 µm, to act as a capacitor with a current flowing therebetween. The electrodes are preferably configured for sensitivity to wellbore mud. The current flowing from either electrode 228a-d,229a-d may be measured as described above. The information gathered preferably provides information sufficient to determine various fluid parameters and/or to identify the type of fluid (e.g., hydrocarbon, mud, etc.) This information may be used for further analysis, for example to provide micro-resistivity imaging of the wellbore. The information may also be used to determine the location and/or characterize reservoirs.

The fluid sensor 120 may be operatively connected to devices for operation therewith. As shown in FIG. 2A1, a downhole sensor 233 may be provided to measure various wellbore parameters. A transceiver 239 may also be provided for communication with the fluid sensor 120a. For example, the transceiver 239 may communicate wirelessly with the logging tool 112 (see FIG. 1). A communication link may also be provided with a wired connection between the fluid sensor 120 and the logging tool 112. The fluid sensor 120 may communicate with the surface unit 114 directly, or via the downhole tool 104.

FIGS. 2A1, 2A2 and 2A3 depict a fluid sensor 120a with a complimentary, dual-comb configuration. Each electrode 228a,229a has a plurality of prongs or teeth 234a,235a extending perpendicularly from a linear band 236a,237a. The prongs 234a,235a of each electrode are interlaced. In this complimentary configuration, the prongs 235a of electrode 228a are positioned adjacent to the prongs 235a of electrode 229a. The prongs 234a are linearly aligned with the prongs 235a such that the prongs 234a,235a alternate. A channel 238 extends between the prongs 234a,235a for the flow of fluid therethrough.

FIG. 2A2 is a cross-sectional view of the fluid sensor of FIG. 2A1 taken along line 2A2-2A2. As shown in this view, the electrodes 228a,229a have a rectangular cross section. The cross section of each prong is preferably about 1 mm² or less. The ratio of the capacitances in this case may roughly be in the ratio of about 1:4.

Figure 3:
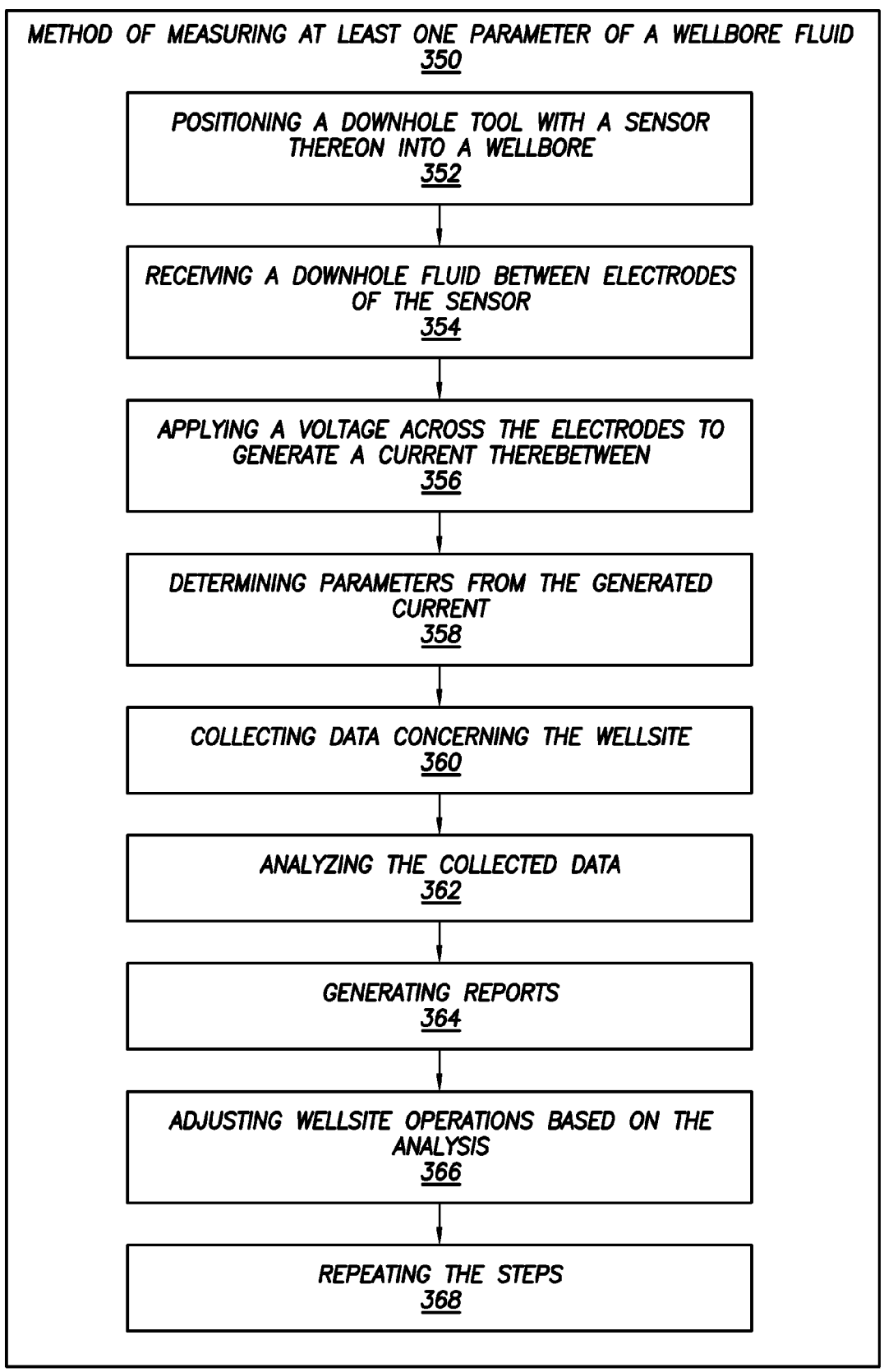

FIG. 2A3 shows an alternate version of the electrodes 228a',229a'. The prongs 234a', 235a' of these electrodes are provided with a rounded cross section. The ratio of the capacitances in this case may roughly be in the ratio of about 1:π. The electrodes may also be provided with other cross sectional geometries, such as planar (not shown). The ratio of capacitances for a fluid sensor having planar PCB type prongs may be about 50%.

FIG. 2B depicts a fluid sensor 120b with an interlocked, multi-comb configuration. In this configuration, each electrode 228b,229b has a linear band 236b,237b with a plurality of primary prongs 240,241 extending perpendicularly therefrom. Each primary prong 240,241 has a plurality of secondary prongs 234b,235b extending perpendicularly therefrom. The primary prongs 240,241 and secondary prongs 234b, 235b are interlaced such that the primary prongs of each electrode alternate and the secondary prongs of each electrode alternate.

The inner primary prongs 240,241 have secondary prongs 234b,235b extending from both sides thereof. The outer primary prongs 240 have secondary prongs 234b extending from one side thereof. In this configuration, the linear portion and the outer prongs of electrode 229b are interlaced such that they wrap around electrode 228b with the electrode 229b positioned around electrode 228b. Additionally, portions of electrode 229b are adjacent both sides of electrode 228b such that portions of the electrode 229b is positioned on either side of electrode 228b. In this configuration, electrode 228b is interlocked with electrode 229b.

FIG. 2C depicts a fluid sensor 120c with an interlocked, round spiral configuration. The electrodes 228c,229c are positioned in an adjacent rounded spiral configurations extending from a central position 242. In this configuration, electrode 228c is interlaced such that it wraps around electrode 229c with the electrode 228c positioned around electrode 229c. Additionally, portions of electrode 228c are adjacent both sides of electrode 229c such that portions of the electrode 228c are positioned on either side of electrode 229c. In this configuration, electrode 228c is interlocked with electrode 229c.

FIG. 2D depicts a fluid sensor 120d with an interlocked, rectangular spiral configuration. The electrodes 228d,229d are positioned in an adjacent rectangular spiral configuration extending from a central position 242. In this configuration, electrode 228d is interlaced such that it wraps around electrode 229d with the electrode 228d positioned around electrode 229d. Additionally, portions of electrode 228d are adjacent both sides of electrode 229d such that portions of the electrode 228d are positioned on either side of electrode 229d. In this configuration, electrode 228d is interlocked with electrode 229d.

FIG. 3 is a flow chart depicting a method (350) of determining at least one parameter of a wellbore fluid. The method involved positioning (352) a downhole tool 104 with a fluid sensor 120 thereon into a wellbore 106 (see, e.g., FIG. 1). A downhole fluid 108 is received (354) between electrodes of the fluid sensor 120. A voltage is applied (356) across electrodes 228a-d, 229a-d of the fluid sensor 120 to generate a current therebetween (see, e.g., FIGS. 2A-2D). Parameters may be determined (358) from the current generated from the electrodes.

Data may be collected (360) concerning the wellsite. This data may be data from the fluid sensor 120, the downhole sensor 233, historical or other data. The sensor collected data may be analyzed (362) and reports generated (364). Action, such as adjusting wellsite operations, may be taken (366) based on the analysis. The steps of the method may be repeated (368) continuously or at discrete locations as the downhole tool 104 is moving through the wellbore. Various combinations of the steps of the method may be performed in a desired order using one or more downhole tools 104 and/or one or more fluid sensors 120.

It will be understood from the foregoing description that various modifications and changes may be provided. For example, the one or more fluid and/or other sensors may be positioned about the wellsite to measure and/or collect data.

This description is intended for purposes of illustration only and should not be construed in a limiting sense. The scope of this invention should be determined only by the language of the claims that follow. The term "comprising" within the claims is intended to mean "including at least" such that the recited listing of elements in a claim are an open group. "A," "an" and other singular terms are intended to include the plural forms thereof unless specifically excluded.

What is claimed is:

1. A fluid sensor for determining at least one parameter of a fluid of a wellbore, the fluid sensor comprising:
a base positionable in the wellbore, the base comprising insulation; and
a pair of electrodes operatively positioned in the insulation, the pair of electrodes having a first of the pair of electrodes interlaced with a second of the pair of electrodes such that at least a portion of the second of the pair of electrodes is surrounded by the first of the pair of electrodes, and wherein a space therebetween the first pair of electrodes and the second pair of electrodes is suitable for passage of the wellbore fluid therethrough, and wherein a capacitance between the portion of the second pair of electrodes surrounded by the first pair of electrodes is based on a cross-sectional shape of the second pair of electrodes and wherein the capacitance has a ratio of approximately 1:4 or 1:$\pi$;
wherein a voltage applied across the pair of electrodes generates a current therebetween whereby at least one parameter of the wellbore fluid passing therethrough may be determined.

2. The fluid sensor of claim 1, wherein each of the pair of electrodes has a first linear portion with a plurality of prongs extending therefrom, the pair of electrodes position adjacent to each other such that the plurality of prongs of each of the pair of electrodes are positioned in an alternating sequence.

3. The fluid sensor of claim 1, wherein each of the pair of electrodes has a first linear portion with a plurality of primary prongs extending therefrom, each primary prong having a plurality of secondary prongs extending therefrom, the pair of electrodes positioned adjacent each other such that the first of the pair of electrodes wrap around the second of the pair of electrodes to interlock therewith.

4. The fluid sensor of claim 1, wherein each of the pair of electrodes are in a round spiral configuration, the pair of electrodes positioned adjacent each other such that the first of the pair of electrodes wraps around at least a portion of the second of the pair of electrodes to interlock therewith.

5. The fluid sensor of claim 1, wherein each of the pair of electrodes are in a rectangular spiral configuration, the pair of electrodes positioned adjacent each other such that the first of the pair of electrodes wraps around at least a portion of the second of the pair of electrodes to interlock therewith.

6. The fluid sensor of claim 1, further comprising a power source for providing the voltage.

7. The fluid sensor of claim 1, further comprising a processor for analyzing the current to determine the at least one fluid parameter.

8. The fluid sensor of claim 1, at least one wellsite sensor operatively connected thereto for determining at least one parameter of the wellbore.

9. The fluid sensor of claim 1, wherein the at least one parameter of the wellbore fluid is one of impedivity, resistivity, impedance, general conductivity, complex conductivity, complex permittivity and/or tangent delta, and combinations thereof.

10. The fluid sensor of claim 1, wherein the base is positionable in the wellbore via a downhole tool.

11. The fluid sensor of claim 10, wherein the downhole tool is operatively connected to a surface unit for communication therewith.

12. The fluid sensor of claim 10, wherein the downhole tool is one of a drilling tool, a wireline tool, a production tool, monitoring tool, a production monitor, a coiled tubing tool, a casing tool and combinations thereof.

13. A method for determining at least one parameter of a fluid in a wellbore, the method comprising:

providing a fluid sensor comprising:
- a base positionable in the wellbore, the base comprising insulation; and
- a pair of electrodes operatively positioned in the insulation, the pair of electrodes having a first of the pair of electrodes interlaced with a second of the pair of electrodes such that at least a portion of the second of the pair of electrodes is surrounded by the first of the pair of electrodes, and wherein a space therebetween the first pair of electrodes and the second pair of electrodes is suitable for passage of the wellbore fluid therethrough, and wherein a capacitance between the portion of the second pair of electrodes surrounded by the first pair of electrodes is based on a cross-sectional shape of the second pair of electrodes and wherein the capacitance has a ratio of approximately 1:4 or 1:$\pi$;

positioning a downhole tool into the wellbore with the fluid sensor thereon;

receiving a downhole fluid in the space between the pair of electrodes;

applying a voltage across the pair of electrodes to generate a current in the space; and determining the at least one fluid parameter of the downhole fluid passing through the space based on the generated current.

14. The method of claim 13, further comprising analyzing the at least one fluid parameter.

15. The method of claim 14, further comprising adjusting at least one wellsite operation based on the analyzed at least one fluid parameter.

* * * * *